US00PP11050P

United States Patent [19]

Adams et al.

[11] Patent Number: Plant 11,050

[45] Date of Patent: Sep. 7, 1999

[54] GLOBBA PLANT NAMED 'PUREST ANGEL'

[76] Inventors: Gregory A. Adams, P.O. Box 4245; Mark L. Collins, P.O. Box 4099, both of Hilo, Hi. 96720

[21] Appl. No.: 09/002,238

[22] Filed: Dec. 31, 1997

[51] Int. Cl.[6] ..... A01H 5/00

[52] U.S. Cl. ..... Plt./263

[58] Field of Search ..... Plt./68.1, 263

*Primary Examiner*—Howard J. Locker
*Assistant Examiner*—Kent L. Bell
*Attorney, Agent, or Firm*—Seth M. Reiss

[57] ABSTRACT

A new and distinct variety of Globba plant characterized by white bracts and divided, mostly transparent bracteoles with upper portion being streaked with red-purple and lower portion with yellow-green. The foliage displays reddish underleaves.

2 Drawing Sheets

CROSS-REFERENCE TO RELATED APPLICATIONS

This application is co-pending with U.S. Plant patent application Ser. Nos. 09/002,231, 09/002,239, and 09/001, 818 drawn to cultivars 'Pristina Pink', 'Ruby Queen', and 'Blushing Maiden', respectively. Being of the same Genus and species, all four cultivars demonstrate similar growth habits and life cycles. The plants are distinct, one from the other, in their bract color; the instant cultivar exhibiting persistent white bracts compared to the light pink bracts of 'Pristina Pink', the dark pink bracts of 'Ruby Queen', and the white and pink two-tone bracts of 'Blushing Maiden'.

BACKGROUND

This new Globba 'Purest Angel' was selected by applicants from the seedling progeny from a cross of unknown parents of *Globba winitii* by applicants at Jungle Jewels, Hi., Kurtistown, Hi., USA. This particular seedling was selected by the applicants in 1994 for propagation and testing because of the distinctive white bracts and reddish underleaves. The selected plant was propagated asexually by cuttings and tissue culture and successive generations maintained the unique features of this new variety. Tissue culture was preformed in a lab in Apopka, Fla. The plant was then grown to maturity in greenhouses in Kurtistown, near Hilo, Hi.

BRIEF SUMMARY OF INVENTION

'Purest Angel' is a low growing deciduous herbaceous perennial with multiple showy pendulous inflorescences. The life cycle of this variety consists of numerous reed like leafy stems emerging in April–May with vigorous growth until flowering commences from July through November with persistent white bracts. In December complete foliar senescence will proceed with a rest period until the following growing season, unless supplemental lighting is applied, therefore extending the flowering period.

BRIEF DESCRIPTION OF PHOTOGRAPHS

Figure 1:
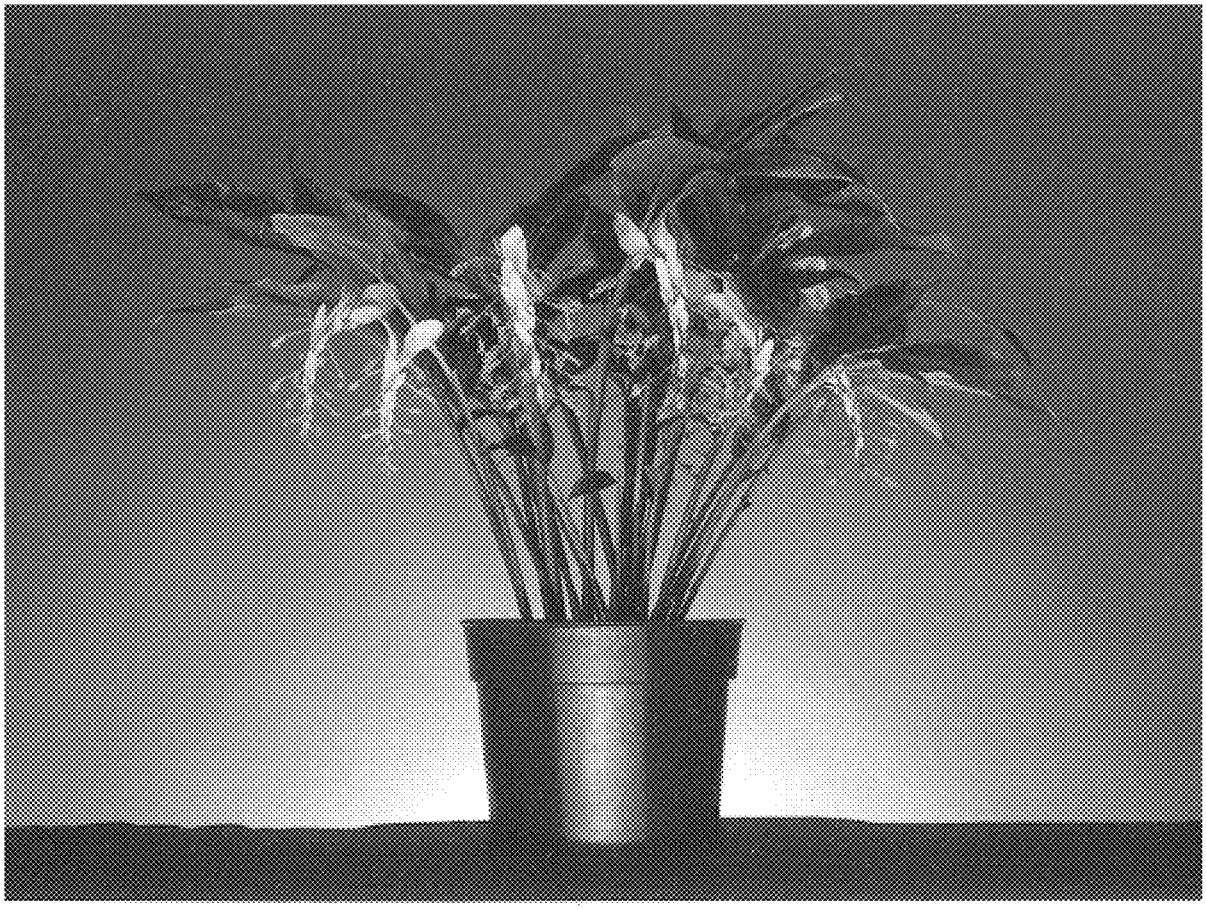

The accompanying color photographs show:

FIG. 1. Depicts the plant form and size and the display of inflorescence.

Figure 2:
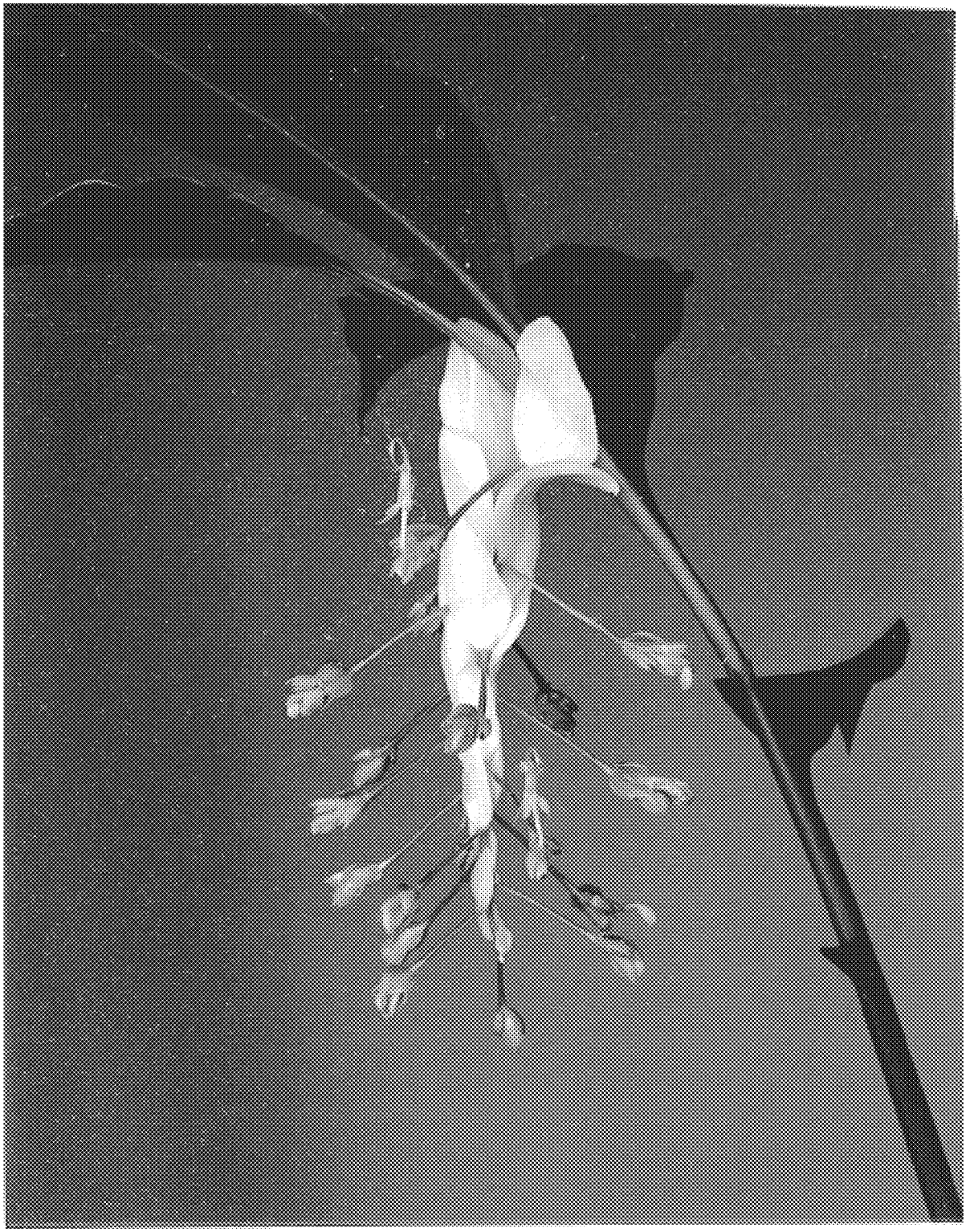

FIG. 2. A side view of a fully open inflorescence depicting bract and leaf color of 'Purest Angel', having flowers extending out of three of the corollas.

The colors are a nearly true as reasonably possible in color illustrations of this type.

DETAILED BOTANICAl DESCRIPTION

In the following botanical description color references are made to The Royal Horticultural Society Colour Chart. Descriptions are based on observations made during 1996 of randomly selected well fertilized clones, grown from fully developed rhizomes, which will yield maxmum height and maturity of this variety. 'Purest Angel' was grown in greenhouse conditions in Kurtistown, Hi. under 55% shaded nursery conditions.

Name: 'Purest Angel'.
Botanical name: *Globba winitii.*
Family: Zingiberaceae.
Commercial use: Potted flowering ornamental plant.
Botanical description: Perennial herb with slender fleshly rhizome, fibrous roots and reed-like leafy stems. Leaves elliptic-lanceolate, attenuate at base, alternate. The top two terminate leaves per pseudostem appear petioled, while the lower leaves are sheathed and appear more sessile in nature. Inflorescence a pendulous terminal raceme, bracts showy; flowers born in cincinni on slender branchlets arising from axils of bracts; bracteoles ovate and open to base; calyx funnelform, 3-lobed; corolla exeeding calyx; 3 petals, small subequal, posterior petal spurred; lip fused into tube with stamen above attachment of lateral staminodes and petals, 2 lobed deflexed; staminodes petaloid, equal or exceeding petals; 1 fertile stamen, filament long and curved, anther with two small triangular appendages on each side, ovary 1 celled with several ovules. The number of bracts and bracteoles per inflorescence vary with the maturity of the cultivar. An immature cultivar, during the flowering period of its second growing season, can be expected to exhibit, on average, between 5 and 12 bracts per inflorescence as well as between 5 and 12 bracteoles per inflorescence. A mature cultivar, during the flowering period of its third and subsequent growing seasons, may exhibit, on average, between 12 and 20 bracts per inflorescence and between 12 and 20 bracteoles per inflorescence. Flowers last a single day. On averge, 6 to 8 actual flowers are produced per branchlet in cincinni each growing season. In a given growing season, an immature plant may exhibit anywhere from 35 to 84 flowers per inflorescence, while a mature plant exhibits from 84 to 140 flowers per inflorescence. Fruit; a small dehiscent capsule with arillate seed with hemispherical protruberances on the outer exocarp.
Plant characteristics:
*Average mature height.*—41 cm.

*Average mature spread.*—61 cm.
*Leaf attitude.*—Arching.
*Leaf length.*—12–16 cm.
*Leaf width.*—4–5.5 cm.
*Leaf color* (*surface and midrib*).—Upper: Green 131A. Lower: Greyed purple 187B.
*Leaf texture.*—Smooth.
*Leaf shape.*—Elliptic lanceolate.
*Flowering season.*—July through November.
*Inflorescence overall length.*—12.5–14 cm.
*Bract basal* (*largest*).—4 cm×2.5 cm.
*Bract apical* (*smallest*).—0.8 cm×0.5 cm.
*Bract color.*—Green-White 157C.
*Bracteoles color.*—Mostly transparent and divided. Upper: Red-purple 59B streaked. Lower: Yellow-Green 150C.
*Raceme and raceme branchlet color.*—Mostly green 145C with red purple 59B highlights.
*Flower overall height.*—2.2 cm.
*Anther with appendages width.*—0.5 cm.
*Stamen length.*—1.5 cm.
*Flower color.*—Yellow Orange 17B.

Disease resistance: It is not known whether the instant cultivar exhibits special resistance to diseases typical of Globba.

We claim:

1. A new and distinct variety of Globba plant named 'Purest Angel', substantially as herein shown and described, characterized particularly as to novelty by the unique combination of white bracts and reddish underleaves along with its profuse flowering habit.

* * * * *